United States Patent
Dasaratha et al.

(10) Patent No.: US 8,271,209 B2
(45) Date of Patent: Sep. 18, 2012

(54) SPECTRAL SEARCHING METHOD FOR SUBSTANCE IDENTIFICATION

(75) Inventors: Sridhar Venkataraman Dasaratha, Bangalore (IN); Thirukazhukundram Subrahmaniam Vignesh, Bangalore (IN); William Scott Sutherland, Murrieta, CA (US); Young Kyo Lee, San Diego, CA (US)

(73) Assignee: General Electric Company, Niskayuna, NY (US)

( * ) Notice: Subject to any disclaimer, the term of this patent is extended or adjusted under 35 U.S.C. 154(b) by 455 days.

(21) Appl. No.: 12/641,705

(22) Filed: Dec. 18, 2009

(65) Prior Publication Data

US 2011/0153226 A1    Jun. 23, 2011

(51) Int. Cl.
   G06F 19/00    (2011.01)
(52) U.S. Cl. ............................................. 702/27; 702/76
(58) Field of Classification Search ............... 702/22, 702/27, 76
   See application file for complete search history.

(56) References Cited

U.S. PATENT DOCUMENTS

| | | | |
|---|---|---|---|
| 4,719,582 A | 1/1988 | Ishida et al. | |
| 5,121,337 A * | 6/1992 | Brown | 702/28 |
| 6,341,257 B1 * | 1/2002 | Haaland | 702/27 |
| 6,415,233 B1 * | 7/2002 | Haaland | 702/22 |
| 6,687,620 B1 | 2/2004 | Haaland et al. | |
| 7,254,501 B1 | 8/2007 | Brown et al. | |
| 2003/0195708 A1 | 10/2003 | Brown | |
| 2008/0137082 A1 | 6/2008 | Grun et al. | |
| 2009/0086205 A1 | 4/2009 | Grun et al. | |

OTHER PUBLICATIONS

Structural Verification and Spectral Confirmation; Advanced Chemistry Development / Labs; URL : http://www.acdlabs.com/solutions/specvalid.html; Solutions/ Structure-Spectrum Structural Identification and Confirmation of Substance ID.

* cited by examiner

Primary Examiner — Bryan Bui
(74) Attorney, Agent, or Firm — Joseph J. Christian

(57) ABSTRACT

Methods, systems and computer program products for identifying components of an unknown mixture using spectral analysis techniques. The method includes comparing the spectrum of the unknown mixture with the spectra of library compounds to obtain candidate mixture combinations. A model is generated for each of the candidate mixture combinations based on a modeling metric. A residual spectrum is computed corresponding to each of the candidate mixture combinations by removing the spectrum of each of the compounds of the candidate mixture combination from the spectrum of the unknown mixture. One or more potential compounds are identified by comparing the residual spectrum with the spectrum of library compounds. The potential compounds are added to the candidate mixture combinations to generate an updated list of the candidate mixture combinations. The search algorithm repeats the steps described above on the updated candidate mixture combinations, until a first termination condition is satisfied.

30 Claims, 4 Drawing Sheets

202

| 33% OF THE RAMAN SPECTRA OF 1.3-CYCLO-OCTADIENE, 33% OF THE RAMAN SPECTRA OF 1.5-HEXADIENE AND 33% OF THE RAMAN SPECTRA OF 1.7-OCTADIENE | | | |
|---|---|---|---|
| TOP HITS DETERMINED AFTER 1st COMPARISON | TOP HITS DETERMINED AFTER 2nd COMPARISON | | |
| | FIRST COMPONENT | SECOND COMPONENT | MAE SCORE |
| ISOPRENE | 1.5 - HEXADIENE | 1.3 - CYCLOOCTADIENE | 1.65 |
| 1.7 - OCTADIENE | 1.7 - OCTADIENE | 1.3 - CYCLOOCTADIENE | 1.91 |
| 1.5 - HEXADIENE | 1 - HEXENE | 1.3 - CYCLOOCTADIENE | 3.38 |
| 1 - HEXENE | 1.5 - HEXADIENE | SORBIC ACID | 3.89 |
| 1 - HEPTENE | 1 - HEPTENE | 1.3 - CYCLOOCTADIENE | 3.98 |
| DIALLYLAMINE | 1.7 - OCTADIENE | SORBIC ACID | 3.99 |
| N - BUTYL ACRYLATE | 1.5 - HEXADIENE | ISOPRENE | 4.11 |
| METHYL UNDECENOATE | 1.7 - OCTADIENE | ISOPRENE | 4.23 |
| ETHYL CINNAMATE | 1.5 - HEXADIENE | MESITYL OXIDE | 4.35 |
| 1 - DODECENE | 1 - HEPTENE | ISOPRENE | 4.35 |

204

| TOP HITS DETERMINED AFTER 3rd COMPARISON | | | |
|---|---|---|---|
| FIRST COMPONENT | SECOND COMPONENT | THIRD COMPONENT | MAE SCORE |
| 1.7 - OCTADIENE | 1.3 - CYCLOOCTADIENE | 1.5 - HEXADIENE | 0.83 |
| 1.5 - HEXADIENE | 1.3 - CYCLOOCTADIENE | 1 - DODECENE | 1.48 |
| 1 - HEXENE | 1.3 - CYCLOOCTADIENE | 1.5 - HEXADIENE | 1.49 |
| 1.5 - HEXADIENE | 1.3 - CYCLOOCTADIENE | 1 - DOCOSENE | 1.50 |
| 1.5 - HEXADIENE | 1.3 - CYCLOOCTADIENE | 1 - DOCOSENE | 1.51 |
| 1 - HEPTENE | 1.3 - CYCLOOCTADIENE | 1.5 - HEXADIENE | 1.51 |
| 1.5 - HEXADIENE | 1.3 - CYCLOOCTADIENE | 1 - DOCOSENE | 1.51 |
| 1.5 - HEXADIENE | 1.3 - CYCLOOCTADIENE | 1 - DOCOSENE | 1.53 |
| 1.5 - HEXADIENE | 1.3 - CYCLOOCTADIENE | 12 -HYDROXYSTEARIC ACID | 1.56 |
| 1.5 - HEXADIENE | 1.3 - CYCLOOCTADIENE | 1 - DOCOSENE | 1.56 |

| 80% OF THE RAMAN SPECTRA OF D-FRUCTOSE, 10% OF THE RAMAN SPECTRA OF PICRIC ACID AND 10% OF THE RAMAN SPECTRA OF CARBAZOLE ||||
|---|---|---|---|
| TOP HITS DETERMINED AFTER 3$^{rd}$ COMPARISON ||||
| FIRST COMPONENT | SECOND COMPONENT | THIRD COMPONENT | MAE SCORE |
| D - FRUCTOSE | NITROBENZENE | CARBAZOLE | 2.68 |
| D - FRUCTOSE | NITROBENZENE | DIMETHYL CARBONATE | 2.72 |
| D - FRUCTOSE | PICRIC ACID | CARBAZOLE | 2.72 |
| D - FRUCTOSE | NITROBENZENE | 2 - IMIDAZOLIDINETHIONE | 2.72 |
| D - FRUCTOSE | NITROBENZENE | SALICYLAMIDE | 2.73 |
| D - FRUCTOSE | NITROBENZENE | BROMOTRICHLOROMETHANE | 2.73 |
| D - FRUCTOSE | PICRIC ACID | DIMETHYL CARBONATE | 2.75 |
| D - FRUCTOSE | NITROBENZENE | P - NITROANILINE | 2.76 |
| D - FRUCTOSE | NITROBENZENE | 1-METHYL-2-PYRROLIDINONE | 2.76 |
| D - FRUCTOSE | PICRIC ACID | 2 - IMIDAZOLIDINETHIONE | 2.76 |

*FIG. 3*

SPECTRAL SEARCHING METHOD FOR SUBSTANCE IDENTIFICATION

BACKGROUND

The present invention relates generally to material identification and, more particularly, to identify components of an unknown mixture using spectral analysis.

Material identification is performed to identify components of an unknown mixture in a wide range of scenarios such as train derailment, overturned vehicles on freeways, leaks, explosions in a chemical plant, illegal drug manufacturing labs and the like. Also, on-site identification of materials is performed in some situations by using sophisticated analytical techniques. Analytical instrumentation such as multi-wavelength infrared and Raman spectrometers, mass spectrometers, nuclear magnetic resonance (NMR) spectrometers, and chromatographic separation-detection systems are typically used for identifying unknown materials. Further, various portable instruments have been developed to provide on-site identification of materials. These instruments use an embedded algorithm for performing material identification. A library of known materials is stored on the instrument and the algorithm identifies the unknown components based on the similarity between the unknown spectra of the material and the stored spectra of the known compounds stored in the library. These methods are generally known as spectral searching methods.

Spectral searching methods typically work well when searching for pure components. However, when mixtures are analyzed using traditional spectral searching methods, the match with the stored materials in the library often indicates a poor match. These problems arise because spectrum of a mixture differs significantly from any of the spectra of pure components of the mixture. This is especially true when there is no single dominant component in the mixture. Since a typical library stores only spectra of pure components that comprise the mixture, many spectral library packages are not well suited for mixture analysis. One approach to overcome this problem is to incorporate spectra of the mixtures into the library. However, the number of possible mixtures that needs to be collected rises exponentially with the number of pure materials in the library. If we further take into account the fact that each of these mixtures would need to be collected at multiple relative concentrations of their constituents, this approach is not feasible other than for libraries of very limited size.

Another approach used for identifying components of an unknown mixture is subtraction based mixture analysis. This involves measuring the spectrum of the unknown mixture, matching the spectrum with the stored spectra of known compounds in the library, subtracting the spectrum of the top match or one of the top matches from the unknown spectrum and repeating the search on the portion of the unknown spectrum (residual spectra) that remains after the subtraction. The residual spectrum contains the spectra of other components of the mixture. In this situation, it is assumed that the top matched compound is always present in the mixture. However, in some cases, it has been observed that the top match may not be a part of the unknown spectrum. Thus, conventional subtraction based approach may not lead to a correct solution in some cases. Also, spectrum of a compound other than the top match may be subtracted thus requiring the user to decide which compound should be subtracted and making this approach impractical for many users.

It would therefore be desirable to have an efficient spectral searching method to identify components of an unknown mixture.

BRIEF DESCRIPTION OF THE INVENTION

The present invention provides methods, systems and computer program products for identifying components of an unknown mixture that overcomes the aforementioned drawbacks. The method employs a search algorithm involving spectral analysis of the spectrum of the unknown mixture.

According to an aspect of the present invention, the method includes comparing the spectrum of the unknown mixture with the spectrum of each of a first plurality of library compounds to obtain one or more candidate mixture combinations. A model is generated for each of the candidate mixture combinations based on a modeling metric. The spectrum of the unknown mixture is fitted as a function of the spectrum of each of the compounds of the candidate mixture combination to generate a fitted spectrum. The fitted spectrum of the candidate mixture combination is removed from the spectrum of the unknown mixture to compute a corresponding residual spectrum for each candidate mixture combination. One or more potential compounds are identified by comparing the residual spectrum with the spectrum of each of a second plurality of library compounds. The potential compounds are added to the candidate mixture combinations to generate new candidate mixture combinations. An updated list of candidate mixture combinations is generated which contains one or more new candidate mixture combinations. The search algorithm repeats the steps described above on the candidate mixture combinations present in the updated list, until a first termination condition is satisfied. Finally, the candidate mixture combinations are presented as the results of the search algorithm.

These and other advantages and features will be more readily understood from the following detailed description of preferred embodiments of the invention that is provided in connection with the accompanying drawings.

BRIEF DESCRIPTION OF THE DRAWINGS

FIG. 2 illustrates an example case in the present invention in which the components of a test mixture are identified;

FIG. 3 illustrates another example case in the present invention in which the components of a test mixture are identified.

DETAILED DESCRIPTION

Various embodiments of the present invention will be described in detail below with reference to accompanying drawings. It will be apparent, however, that these embodiments may be practiced without some or all of these specific details. In other instances, well known process steps or elements have not been described in detail in order not to unnecessarily obscure the description of the invention. The following example embodiments and their aspects are described and illustrated in conjunction with apparatuses, methods, and systems which are meant to be illustrative examples, not limiting in scope.

The invention provides a method of identifying components of an unknown mixture using analysis of the spectrum of the unknown mixture. The method includes a search algorithm involving repeated steps to obtain a set of compounds that may be present in the unknown mixture. The search algorithm may be incorporated in various spectrometers such as, but not limited to, multi-wavelength infrared and Raman spectrometers, mass spectrometers, nuclear magnetic resonance (NMR) spectrometers, and chromatographic separation-detection systems for identifying components of the unknown mixture.

Figure 1:
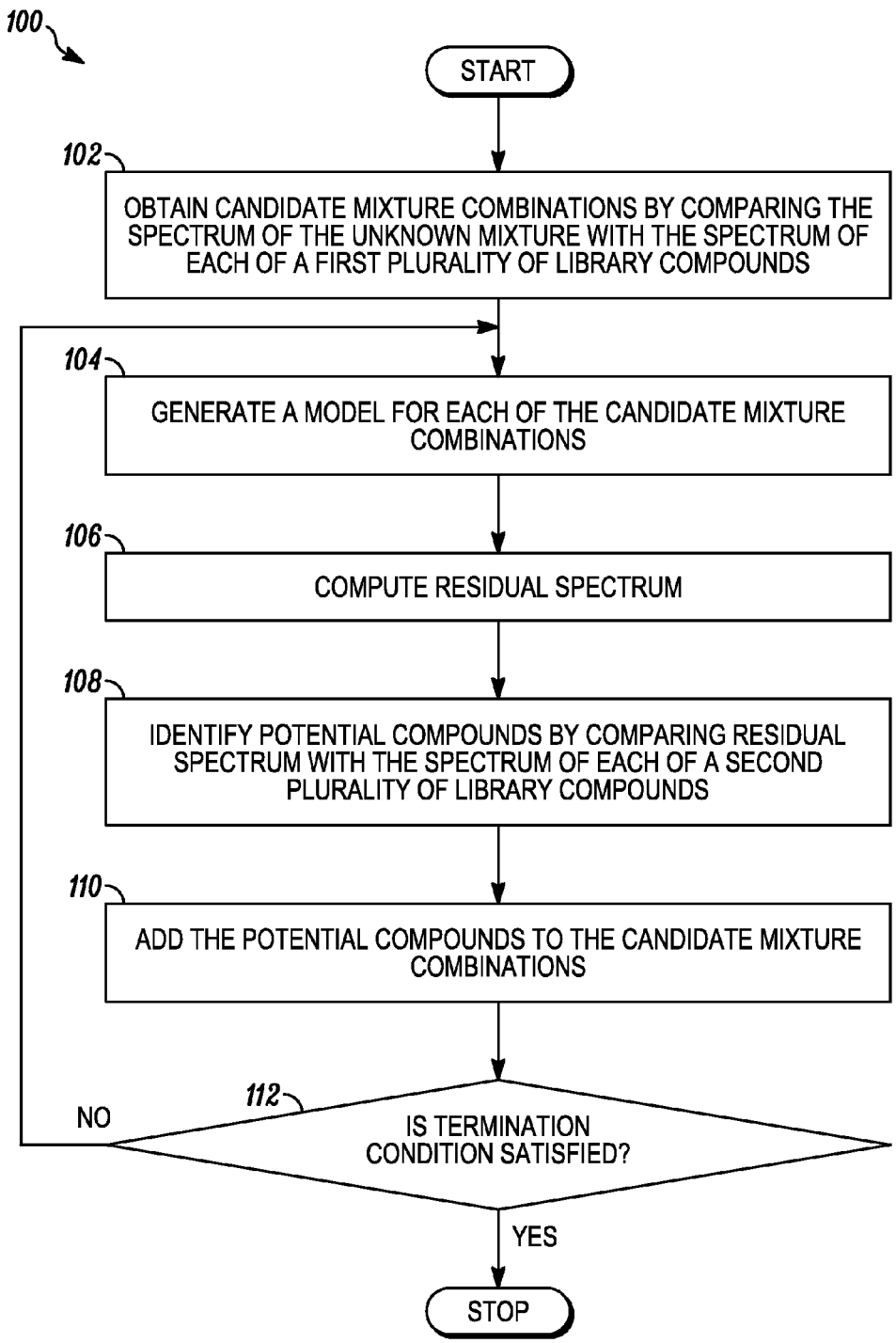
FIG. 1 is a flowchart illustrating an example method for identifying components of a mixture according to an embodiment of the present invention.

FIG. 1 illustrates a flowchart 100 summarizing various steps involved in an example embodiment of the invention. In various embodiments of the present invention, a search algorithm is employed to identify one or more compounds that may be present in an unknown mixture. At step 102, the spectrum of the unknown mixture is compared with the spectrum of each of a first plurality of library compounds. The library may contain the spectrum of one or more known compounds. In an embodiment of the invention, the library may be stored as various sub-libraries. Further, the user may select one or more sub-libraries to be considered in the search algorithm. For instance, the user may pre-select a portion of the library that may be used as the first plurality of library compounds in the search algorithm. Alternatively, a pre-processing step may be employed to select a portion of the library based on the user input. In one embodiment of the present invention, the mixture may contain more than one compound. Further, the unknown mixture may be a liquid, a solid or a powder.

The spectrum of the unknown mixture may be obtained using various spectroscopic techniques, such as, but not limited to, infrared, Raman, fluorescence and near infrared spectroscopy techniques. In an embodiment of the present invention, before comparing the spectrum of the unknown mixture with the spectrum of the known compounds, the spectrum of the unknown mixture, as well as the spectra of known compounds in the library, may be corrected. The correction is made to remove all undesirable signals and artifacts that are present in the spectrum and are not related to the chemical compositions of the unknown mixture and known compounds. These undesirable signals and artifacts may be present in the spectrum due to various instrumental effects, such as, but not limited to, the transmission of optical elements, the variability of the detector response, and any other non-desired sample effects due to the instrument utilized to obtain the spectra, for example, but not limited to, fluorescence and baseline artifacts in the case of Raman spectra. In an embodiment of the present invention, the spectrum of the unknown mixture may be pre-processed using a Savitzky-Golay filter. However, a person ordinarily skilled in the art may appreciate that the uncorrected spectrum of the unknown mixture may also be utilized to practice the inventive method without departing from the spirit and scope of the present invention.

A similarity measure is computed for the first plurality of library compounds. Various methods such as, but not limited to, Euclidean distance, correlation, Manhattan distance, dot product, mutual information, linear regression, a principal component regression model, and a partial least squares model may be used to compute the similarity measure. Principal component regression models and partial least squares models are built using the library data and then applied to the unknown mixture to generate similarity measures. Further, the first plurality of library compounds may be sorted by the similarity measure and ranked in a descending or ascending order depending on the similarity measure used. A pre-determined number, assume the top 'L', compounds may be selected from the ranked compounds. In another embodiment of the present invention, the compounds having the similarity measure greater than a predetermined threshold value may be selected. In another embodiment, the spectrum of each of the first plurality of library compounds may be regressed against the spectrum of the unknown mixture. A spectral error parameter of a metric may be computed as a similarity measure for each of the first plurality of library compounds. In one embodiment, the first plurality of library compounds may be sorted in an ascending order of the spectral error parameter and ranked. Further, a pre-determined number, assume the top 'M', compounds may be selected from the ranked compounds. In another embodiment of the present invention, the compounds having the spectral error parameter less than a predetermined threshold value may be selected. The spectral error parameter may be computed for various metrics, such as, but not limited to, mean square error (MSE) metric, mean absolute error (MAE) metric, sum of squares error (SSE) metric and Durbin-Watson metric.

The selected compounds are hereinafter referred to as candidate mixture combinations. In one embodiment, during first run of the search algorithm, each candidate mixture combination consists of only one compound. For example, when 'L' is equal to 10, the number of candidate mixture combinations is also 10. In other embodiments of the present invention, candidate mixture combinations may be formed by generating binary combinations of the selected compounds. For example, when 10 compounds are selected based on the similarity measure, 45 binary combinations of the compounds may be obtained. Thus, a total of 45 candidate mixture combinations, each containing two compounds, may be obtained. In an alternative embodiment of the present invention, stochastic methods such as, but not limited to, genetic algorithms may be used to obtain candidate mixture combinations of any size.

At step 104, a model is generated for each of the candidate mixture combinations obtained in the step 102. The model is used to generate scaling factors for each of the compounds present in the candidate mixture combination. The scaling factors may also be determined through a manual process or based on prior knowledge and experience. Various methods, such as, but not limited to, multivariate least squares regression, non-negative multivariate least squares regression, partial least squares regression, principal component regression algorithm, Bayesian regression, least absolute deviation regression and least median square regression may be used to estimate the scaling factor. The regression method used for estimating the scaling factor may depend on one or more parameters. For example, when the spectral noise is not homoscedastic white noise, multivariate generalized least squares regression may be used. Similarly, when the components of the mixture are spectrally similar, ridge regression-based estimates or principal components-based regression may be used. In other embodiments of the present invention, non-linear regression methods such as, but not limited to, Nadaraya Watson estimators and Kernel regression may be used wherein the scaling factor depends on the magnitude of the spectral intensity. Further, when a scaling factor is dependent upon the spectral bin, other methods such as, Bayesian regression, piece-wise regression, local regression and spline smoothing-based regression may be used to estimate the scaling factor.

In an embodiment of the present invention, a regression model may be generated by fitting the spectrum of each of the compounds present in the candidate mixture combination against the spectrum of the unknown mixture. For example, if the candidate mixture combination consists of compounds [A, B and C] and the unknown mixture is Z then S(Z) is fitted as a function of the S(A), S(B) and S(C), where S(Z) is spectrum of the unknown mixture, S(A) is spectrum of the compound A and so on. In one embodiment of the present invention, a fitted spectrum may be generated for each candidate mixture combination by fitting the spectrum of each of the compounds of the candidate mixture combination against the spectrum of the unknown mixture. In other words, regression model may be generated to fit the spectrum of the unknown mixture as a function of the spectrum of each of the compounds present in the candidate mixture combination. Various modeling metrics may be used for generating the model, such as, but not limited to, mean square error (MSE) metric, mean absolute error (MAE) metric, sum of squares error (SSE) metric and Durbin-Watson metric.

In one embodiment, all the candidate mixture combinations may be selected for further analysis in the next step of the algorithm. In another embodiment, one or more candidate mixture combinations may be selected for further analysis in the next step based on a spectral error parameter of a metric. A spectral error parameter may be computed for each of the candidate mixture combinations. Further, the candidate mixture combinations may be sorted in an ascending order of the spectral error parameter and ranked. Various metrics, such as, but not limited to, mean square error (MSE) metric, mean absolute error (MAE) metric, sum of squares error (SSE) metric and Durbin-Watson metric may be used for selecting the candidate mixture combinations. A pre-determined number of top candidate mixture combinations may be selected from the ranked candidate mixture combinations. Thus, only selected candidate mixture combinations may be used for further analysis in the next step of the search algorithm. In an embodiment of the present invention, same metric may be used for fitting the regression model and ranking the candidate mixture combinations. In another embodiment of the present invention, different metrics may be used for fitting the regression model and ranking the candidate mixture combinations.

At step 106, a residual spectrum may be computed for each of the candidate mixture combinations by removing the fitted spectrum of the candidate mixture combination from the spectrum of the unknown mixture. In an embodiment of the present invention, the residual spectrum may be computed by subtracting the fitted spectrum obtained in step 104 from the spectrum of the unknown mixture. In other embodiments of the present invention, peak-based subtraction may be used to remove the fitted spectrum of the candidate mixture combination from the spectrum of the unknown mixture.

At step 108, the residual spectrum corresponding to each candidate mixture combination is compared with the spectrum of each of a second plurality of library compounds. In an embodiment of the invention, the second plurality of library compounds used in this step is same as the first plurality of library compounds used in step 102. The second plurality of the compounds may be selected by the methods used for selection of first plurality of the compounds in the step 102. In an embodiment of the present invention, a similarity measure may be computed for each of the second plurality of library compounds. Various methods such as, but not limited to, Euclidean distance, correlation, Manhattan distance, dot product, mutual information, a principal component regression model, and a partial least squares model may be used to compute the similarity measure. Principal component regression models and partial least squares models are built using the library data and then applied to the unknown mixture to generate similarity measures. In an embodiment of the invention, the second plurality of library compounds may be sorted by the similarity measure and ranked in a descending or ascending order depending on the similarity measure used. Further, a pre-determined number, assume the top 'N', compounds may be selected from the ranked compounds. Hereinafter, the candidate mixture combination is interchangeably referred to as the "parent" mixture combination. In another embodiment of the present invention, the compounds that have the similarity measure greater than a predetermined threshold value may be selected.

In another embodiment, the spectrum of each of the second plurality of library compounds may be regressed against the residual spectrum. A spectral error parameter of a metric may be computed as a similarity measure for the second plurality of library compounds. In one embodiment, the second plurality of library compounds may be sorted in an ascending order of the spectral error parameter and ranked. Further, a pre-determined number, assume the top 'T', compounds may be selected from the ranked compounds. In another embodiment of the present invention, the compounds having the spectral error parameter less than a predetermined threshold value are selected. The spectral error parameter may be computed for various metrics, such as, but not limited to, mean square error (MSE) metric, mean absolute error (MAE) metric, sum of squares error (SSE) metric and Durbin-Watson metric.

The selected compounds are hereinafter referred to as potential compounds. Thus, the potential compounds are identified based on the comparison of the residual spectrum of each of the candidate mixture combination with the spectrum of the second plurality of library compounds. The potential compounds are interchangeably referred to as the "children" potential compounds of the corresponding "parent" mixture combination. Thus, for each "parent" mixture combination, a set of "children" potential compounds are identified in step 108.

At step 110, the potential compounds are added to the candidate mixture combinations. In an embodiment of the present invention, one or more new candidate mixture combinations may be obtained by the addition of "children" potential compounds to the "parent" mixture combinations. In an exemplary embodiment of the present invention, each "children" potential compound may be added to the corresponding "parent" mixture combination. In other embodiments of the present invention, "children" potential compounds of other "parent" mixture combinations may be added to a "parent" mixture combination. Thus, addition of the "children" potential compounds to the "parent" mixture combinations results in the new candidate mixture combinations.

Further, a spectral error parameter may be calculated for each of the new candidate mixture combinations. In an embodiment of the present invention, the new candidate mixture combinations may be sorted in an ascending order of the spectral error parameter and ranked. In various embodiments of the present invention, the spectral error parameter may be computed for various metrics, such as, but not limited to, sum of square error (SSE) metric, mean square error (MSE) metric, mean absolute error (MAE) metric and Durbin-Watson metric. In one embodiment of the present invention, mean absolute error (MAE) metric may be used for sorting and ranking the new candidate mixture combinations. In an embodiment of the present invention, a pre-determined number, assume top 'T', candidate mixture combinations may be selected from the ranked list of the new candidate mixture combinations. In another embodiment of the present invention, the candidate mixture combinations that have the spectral error parameter less than a threshold value are selected.

Thus, an updated list of the candidate mixture combinations consisting of the selected candidate mixture combinations is generated.

At step 112, the search algorithm checks a first termination condition and determines whether another iteration of the algorithm is required. The search algorithm terminates when the first termination condition is satisfied. In an embodiment of the present invention, the termination condition is completion of a fixed number of iterations selected by an operator. In another embodiment of the present invention, the search algorithm may be terminated when no significant improvement in the spectral error parameters is observed. For example, the search may be terminated when less than 5% reduction in the MAE metric is achieved by any of the candidate mixture combinations in the updated list as compared to the candidate mixture combinations generated in the previous step. In yet another embodiment of the present invention, the search algorithm may be terminated when the spectral error parameter of any of the candidate mixture combinations is less than a threshold value. The search algorithm may also be terminated when a goodness of fit measure such as the coefficient of determination (R2) exceeds a certain value. If the first termination condition is not satisfied, then steps 104 to 112 are repeated for identifying other components of the unknown mixture.

When first termination condition is satisfied, the search algorithm is terminated and results of the search algorithm may be presented to the user. In an exemplary embodiment of the present invention, the output of the search algorithm may be a single candidate mixture combination with corresponding spectral error parameter such as [A, B, C . . . Score X]. For example, A, B and C may refer to the compounds of the candidate mixture combination and X may refer to the mean absolute error (MAE) score of the candidate mixture combination. In some embodiments of the present invention, the output of the search algorithm may be multiple candidate mixture combinations with corresponding spectral error parameters such as [A, B, C . . . Score X] [A, B, D . . . Score Y]. Multiple candidate mixture combinations may be presented in various another ways such as [A, B/C/D, E/F]. In other embodiments of the present invention, the output of the search algorithm may be a set of possible compounds present in the unknown mixture such as [A, B, C, D, E, F, G]. Thus, the search algorithm may provide a reduced set of compounds that may be present in the unknown mixture.

In one embodiment, the unknown mixture may contain only one compound. The spectrum of the unknown mixture is compared with the spectrum of each of a first plurality of library compounds. A similarity measure is computed for each of the first plurality of library compounds. Based on the similarity measure, one or more compounds may be selected from the first plurality of library compounds. The selected compounds are hereinafter referred to as candidate mixture combinations. In this embodiment, each candidate mixture combination contains only one compound. In one embodiment, the search algorithm is terminated after this step if a second termination condition is satisfied. For example, the search algorithm may be terminated if the similarity measure of a candidate mixture combination is greater than a predetermined threshold. Further, the candidate mixture combinations satisfying the second termination condition are presented as the results of the search algorithm to the user.

If the second termination condition is not satisfied, then the algorithm moves to the next step i.e. generating a model for each of the candidate mixture combinations based on a modeling metric and a fitted spectrum is obtained for each candidate mixture combination. Further, a residual spectrum is computed for each of the candidate mixture combinations. Each residual spectrum is compared with the spectrum of each of a second plurality of library compounds to identify one or more potential compounds that may be present in the unknown mixture. Each potential compound may be added to the corresponding candidate mixture combination to obtain a set of new candidate mixture combinations. In one embodiment, the new candidate mixture combinations may be sorted and ranked based on a spectral error parameter. In various embodiments of the present invention, the spectral error parameter may be computed for various metrics, such as, but not limited to, sum of squares error (SSE) metric, mean square error (MSE) metric, mean absolute error (MAE) metric and Durbin-Watson metric. One or more candidate mixture combinations may be selected from the ranked list of the candidate mixture combinations. In one embodiment, an updated list of candidate mixture combinations containing the top 'P' candidate mixture combinations is generated. The search algorithm may check a first termination condition and determine whether another iteration of the algorithm is required. Further, when the first termination condition is satisfied, the search algorithm provides one or more candidate mixture combinations that may be present in the mixture.

FIG. 2 illustrates an example embodiment of the present invention in which the components of an unknown mixture are identified using the search algorithm. Consider a synthetic test mixture spectra created by combining 33% of the Raman spectra of 1.3-Cyclooctadiene, 33% of the Raman spectra of 1.5-Hexadiene and 33% of the Raman spectra of 1.7-Octadiene for illustrating various steps involved in the search algorithm. In practice, the spectrum of the test mixture may be obtained using various spectroscopic techniques, such as, but not limited to, infrared, Raman, fluorescence and near infrared spectroscopy techniques. In an embodiment of the present invention, before comparison of the spectrum of the test mixture with the spectrum of the known compounds, the spectrum of the test mixture, as well as the spectra of known compounds in the library, may be corrected.

The spectrum of the test mixture is compared with the spectrum of each of the first plurality of library compounds. In one embodiment, a similarity measure may be computed for each of the first plurality of library compounds. Various methods such as, but not limited to, Euclidean distance, correlation, Manhattan distance, dot product, mutual information, a principal component regression model, and a partial least squares model may be used to compute the similarity measure. Principal component regression models and partial least squares models are built using the library data and then applied to the unknown mixture to generate similarity measures. Further, the first plurality of library compounds may be sorted by the similarity measure and ranked in a descending or ascending order depending on the similarity measure. In one embodiment, a pre-determined number of the compounds may be selected from the ranked compounds. In another embodiment of the present invention, the first plurality of library compounds having the similarity measure greater than a predetermined threshold value may be selected. Table 202 in the first column, shows the list of top 10 compounds obtained after the first comparison. In another embodiment, the spectrum of each of the first plurality of library compounds may be regressed against the spectrum of the test mixture. A spectral error parameter of a metric may be computed as a similarity measure for each of the first plurality of library compounds. In one embodiment, the first plurality of library compounds may be sorted in an ascending order of the spectral error parameter and ranked. Further, a pre-determined number of the compounds may be selected from the ranked compounds. In another embodiment of the present invention, the compounds having the spectral error parameter less than a predetermined threshold value may be selected. The spectral error parameter may be computed for various metrics, such as, but not limited to, mean square error (MSE) metric, mean absolute error (MAE) metric, sum of squares error (SSE) metric and Durbin-Watson metric.

The selected compounds are hereinafter referred to as candidate mixture combinations. In one embodiment, each candidate mixture combination may contain only one compound. In another embodiment, candidate mixture combinations may be formed by generating binary combinations of the pre-determined number of top compounds from the ranked compounds. In this example, we consider 10 candidate mixture combinations, each containing only one compound as shown in the first column of the table 202. The candidate mixture combinations are interchangeably referred to as the "parent" mixture combinations.

A model is generated for each of the candidate mixture combinations obtained in the previous step. A regression model may be generated by fitting the spectrum of each of the candidate mixture combinations against the spectrum of the test mixture. In an embodiment of the present invention, a scaling factor may be estimated using the regression model generated by fitting the spectrum of each of the candidate mixture combinations against the spectrum of the test mixture. Various modeling metrics may be used for generating the model, such as, but not limited to, mean square error (MSE) metric, mean absolute error (MAE) metric, sum of squares error (SSE) metric and Durbin-Watson metric. In this example, sum of squares error (SSE) metric is used for fitting the spectrum of each of the candidate mixture combinations against the spectrum of the test mixture. In one embodiment of the present invention, a fitted spectrum may be generated for each candidate mixture combination by fitting the spectrum of each of the compounds of the candidate mixture combination against the spectrum of the test mixture. A residual spectrum is computed for each of the candidate mixture combinations by removing the fitted spectrum of the candidate mixture combination from the spectrum of the test mixture. In one embodiment, the residual spectrum may be computed by subtracting the fitted spectrum from the spectrum of the test mixture. In other embodiments of the present invention, peak-based subtraction may be used to remove the spectrum of the candidate mixture combination from the spectrum of the test mixture.

Each residual spectrum is compared with the spectrum of each of the second plurality of library compounds. Various methods such as, but not limited to, Euclidean distance, correlation, Manhattan distance, dot product, mutual information, linear regression, a principal component regression model, and a partial least squares model may be used to identify one or more potential compounds. These methods have been explained in the first step of the search algorithm to obtain the candidate mixture combinations. Hereinafter, the candidate mixture combination is interchangeably referred to as the "parent" mixture combination. In this example, 10 potential compounds are selected from the library compounds. More specifically, for each residual spectrum, 10 potential compounds are selected, hereinafter referred to as the "children" potential compounds of the "parent" mixture combination. Thus, a total of 100 potential compounds are identified for the 10 candidate mixture combinations. In an embodiment of the present invention, one or more new candidate mixture combinations may be obtained by the addition of "children" potential compounds to the "parent" mixture combinations. In an exemplary embodiment of the present invention, each "children" potential compound may be added to the corresponding "parent" mixture combination. In other embodiments of the present invention, "children" potential compounds of other "parent" mixture combinations may be added to a "parent" mixture combination. Thus, a total of 100 new candidate mixture combinations, each containing two compounds, are obtained by the addition of the potential compounds.

Further, a spectral error parameter may be calculated for each of the new candidate mixture combinations. In an embodiment of the present invention, the new candidate mixture combinations may be sorted in an ascending order of the spectral error parameter and ranked. In various embodiments, the spectral error parameter may be computed for various metrics, such as, but not limited to, sum of squares error (SSE) metric, mean square error (MSE) metric, mean absolute error (MAE) metric and Durbin-Watson metric. In an embodiment of the present invention, a pre-determined number of the candidate mixture combinations may be selected from the ranked list of the new candidate mixture combinations. In another embodiment of the present invention, the candidate mixture combinations that have the spectral error parameter less than a threshold value are selected. Thus, an updated list of the candidate mixture combinations consisting of the selected candidate mixture combinations is generated. In this example, spectral error parameter of the mean absolute error (MAE) metric is used for ranking the new candidate mixture combinations. MAE scores are calculated for the 100 new candidate mixture combinations, each containing two compounds. Further, new candidate mixture combinations are sorted and ranked by their MAE scores. Table 202 shows the updated list of the candidate mixture combinations comprising 10 new candidate mixture combinations selected by the search algorithm along with their MAE scores.

The search algorithm is repeated for the candidate mixture combinations present in the updated list of the candidate mixture combinations. Referring to FIG. 1, steps 104 to 112 are repeated for identifying other components of the test mixture. A regression model is generated by fitting the spectrum of the compounds of the candidate mixture combination against the spectrum of the test mixture. In one embodiment of the present invention, a fitted spectrum may be generated for each candidate mixture combination by fitting the spectrum of each of the compounds of the candidate mixture combination against the spectrum of the test mixture. In this example, sum of squares error (SSE) metric is used for fitting the regression models. A residual spectrum is computed for each candidate mixture combination by subtracting the corresponding fitted spectrum from the spectrum of the test mixture. The residual spectrum is compared with the spectrum of each of the second plurality of library compounds. A similarity measure may be calculated for each of the second plurality of library compounds. Further, the second plurality of library compounds are sorted by the similarity measure and ranked in a descending or ascending order depending on the similarity measure used. For each candidate mixture combination, 10 potential compounds are selected from the ranked compounds. Thus, a total of 100 potential compounds are identified for the 10 candidate mixture combinations.

Each potential compound is added to the corresponding candidate mixture combination to generate a total of 100 new candidate mixture combinations. In this example, new candidate mixture combinations are then sorted in an ascending order of the spectral error parameter of the mean absolute error (MAE) metric and ranked. Top 10 candidate mixture combinations are selected from the ranked new candidate mixture combinations. An updated list of candidate mixture combinations comprising top 10 new candidate mixture combinations is generated. Table 204 shows the updated list of the candidate mixture combinations identified by the search algorithm along with their MAE scores. In this example, the first termination condition is completion of two iterations of the search algorithm hence the search algorithm terminates after the second run. The search algorithm may present the top ternary candidate mixture combination and the associated MAE score as the solution.

FIG. 3 illustrates an example embodiment of the present invention in which the components of an unknown mixture are identified using the search algorithm. Consider a synthetic test mixture spectra created by combining 80% of the Raman spectra of D-Fructose, 10% of the Raman spectra of Picric Acid and 10% of the Raman spectra of Carbazole for illustrating various steps involved in the search algorithm. The test mixture contains Picric Acid and Carbazole as the minor components. The spectrum of the test mixture may be obtained using a spectrometer. The test mixture may be pre-processed prior to the start of the search algorithm. In this example, the first termination condition is completion of two iterations of the search algorithm hence the search algorithm terminates after the second run.

Table 302 shows the top 10 candidate mixture combinations identified by the search algorithm. The actual components of the test mixture are at the $3^{rd}$ position in the list of top 10 candidate mixture combinations. In one embodiment, the candidate mixture combinations which have their MAE scores within a fixed percentage of the minimum MAE score may be presented as the search results. In this example, if the fixed percentage is set as 2%, top 6 ternary candidate mixture combinations are presented as the search results. Thus, the search algorithm may provide a list of mixture combinations that may represent the unknown mixture.

Figure 4:
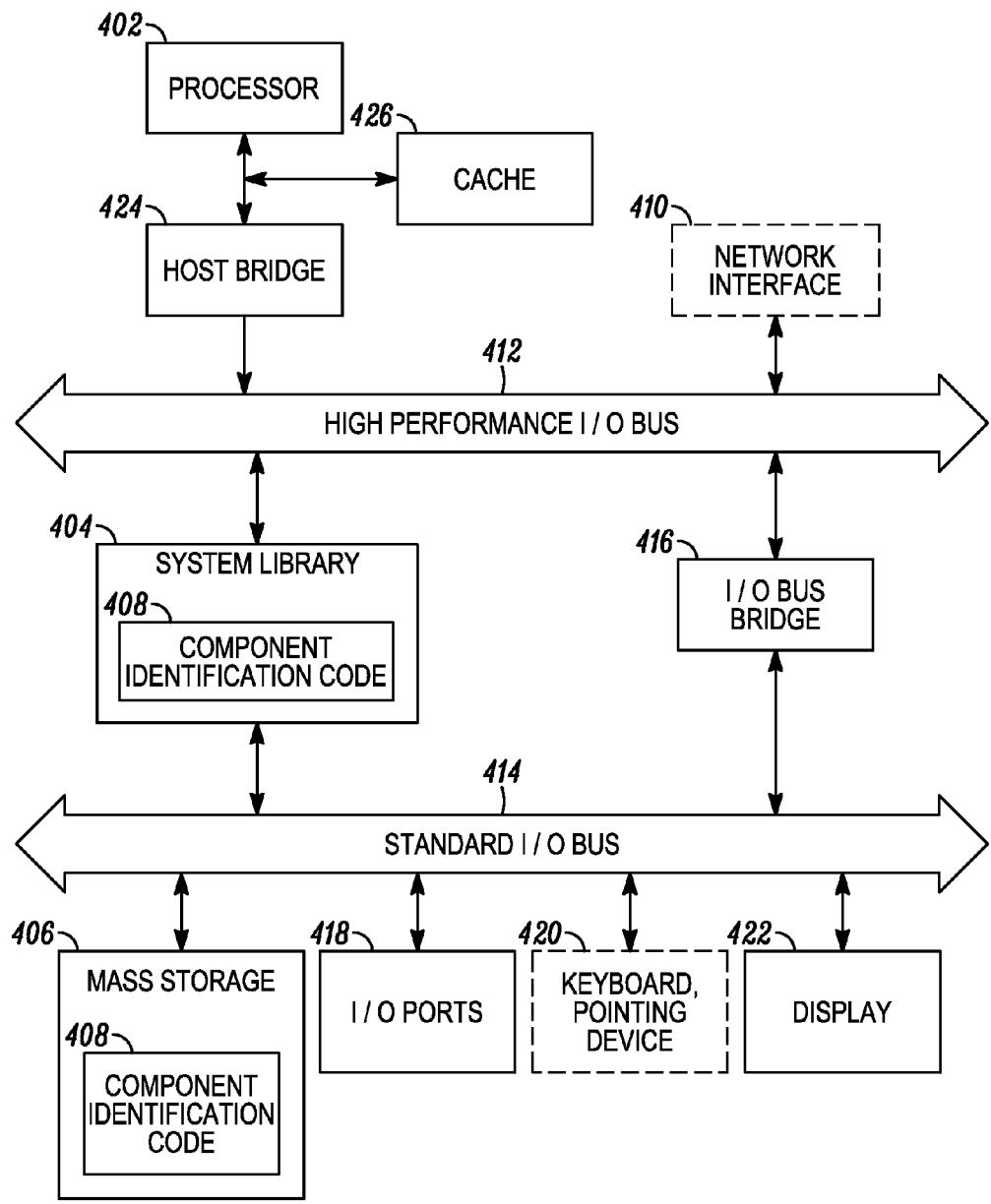
FIG. 4 is a schematic diagram illustrating an example system in which the computer program code of the algorithm is enabled according to an embodiment of the present invention.

FIG. 4 illustrates an example hardware system 400 to implement the component identification system according to one embodiment. Hardware system 400 includes at least one processor 402, a system library 404, and mass storage 406. The system library 404 has stored therein one or more application software, programming instructions for implementing component identification process 408, an operating system and drivers directed to the functions described herein. Mass storage 406 provides permanent storage for the data and programming instructions for component identification process 408, whereas system library 404 (e.g., DRAM) provides temporary storage for the data and programming instructions when executed by processor 402. The process flow of the programming instructions for component identification process 408 is described in detail in conjunction with FIG. 1. A network/communication interface 410 provides communication between hardware system 400 and any of a wide range of networks, such as an Ethernet (e.g., IEEE 802.3) network, etc. Additionally, hardware system 400 includes a high performance input/output (I/O) bus 412 and a standard I/O bus 414. System library 404 and network/communication interface 410 couple to bus 412. Mass storage 406 couple to bus 414. I/O Bus Bridge 416 couples the two buses 412 and 414 to each other.

In one embodiment, component identification process 408 described herein is implemented as a series of software routines run by hardware system 400. These software routines comprise a plurality or series of instructions to be executed by a processor in a hardware system, such as processor 402. Initially, the series of instructions are stored on a storage device, such as mass storage 406. However, the series of instructions can be stored on any suitable storage medium, such as a diskette, CD-ROM, ROM, EEPROM, DVD, Blu-ray disk, etc. Furthermore, the series of instructions need not be stored locally, and could be received from a remote storage device, such as server on a network, via network/communication interface 410. The instructions are copied from the storage device, such as mass storage 406, into system library 404 and then accessed and executed by processor 402.

In one embodiment, hardware system 400 may also include I/O ports 418, a keyboard and pointing device 420, a display 422 coupled to bus 412. I/O ports 418 are one or more serial and/or parallel communication ports that provide communication between additional peripheral devices, which may be coupled to hardware system 400. A host bridge 424 couples processor 402 to high performance I/O bus 412. Hardware system 400 may further include video memory (not shown) and a display device coupled to the video memory. Collectively, these elements are intended to represent a broad category of computer hardware systems, including without limitation general purpose computer systems based on the x86-compatible processors manufactured by Intel Corporation of Santa Clara, Calif., and the x86-compatible processors manufactured by Advanced Micro Devices (AMD), Inc., of Sunnyvale, Calif., as well as any other suitable processor.

Hardware system 400 may include a variety of system architectures; and various components of the hardware system 400 may be rearranged. For example, cache 426 may be on-chip with processor 402. Alternatively, cache 426 and processor 402 may be packed together as a "processor module," with processor 402 being referred to as the "processor core." Furthermore, certain embodiments of the present invention may not require nor include all of the above components. For example, the peripheral devices shown coupled to standard I/O bus 412 may couple to high performance I/O bus 412. In addition, in some embodiments only a single bus may exist with the components of hardware system 400 being coupled to the single bus. Furthermore, hardware system 400 may include additional components, such as additional processors, storage devices, or memories.

An operating system manages and controls the operation of hardware system 400, including the input and output of data to and from software applications (not shown). The operating system provides an interface between the software applications being executed on the system and the hardware components of the system. According to one embodiment of the present invention, the operating system is the LINUX operating system. However, the present invention may be used with other suitable operating systems, such as the Windows® 95/98/NT/XP/Server operating system, available from Microsoft Corporation of Redmond, Wash., the Apple Macintosh Operating System, available from Apple Computer Int. of Cupertino, Calif., UNIX operating systems, and the like.

The present invention has been explained with reference to specific embodiments. For example, while embodiments of the present invention have been described with reference to specific hardware and software components, those skilled in the art will appreciate that different combinations of hardware and/or software components may also be used, and that particular operations described as being implemented in hardware might also be implemented in software or vice versa. Other embodiments will be evident to those of ordinary skill in the art.

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

What is claimed is:

1. A method of spectral searching an unknown mixture, the method comprising:
    obtaining one or more candidate mixture combinations by comparing the spectrum of the unknown mixture with the spectrum of each of a first plurality of library compounds;
    generating a model for each of the candidate mixture combinations based, at least in part, on a modeling metric;
    computing a residual spectrum corresponding to each of the candidate mixture combinations by removing the spectrum of each of the compounds of the candidate mixture combination from the spectrum of the unknown mixture;
    identifying one or more potential compounds by comparing each residual spectrum with the spectrum of each of a second plurality of library compounds;
    adding the potential compounds to the candidate mixture combinations to generate an updated list of the candidate mixture combinations; and
    repeating the generating of the model, computing of the residual spectrum, identifying of the potential compounds, and adding of the potential compounds until a first termination condition is satisfied.

2. The method of claim 1, wherein the first and second plurality of library compounds are selected from a portion of the library.

3. The method of claim 2, wherein the portion of the library is selected by a user.

4. The method of claim 1, wherein obtaining the candidate mixture combinations comprises computing a similarity measure for the first plurality of library compounds.

5. The method of claim 4, wherein the similarity measure is computed using at least one of Euclidean distance, Manhattan distance, dot product, correlation, mutual information, linear regression, principal component regression, and partial least squares regression.

6. The method of claim 4, wherein obtaining the candidate mixture combinations further comprises ranking the first plurality of library compounds based on the similarity measure and selecting a pre-determined number of top ranked compounds.

7. The method of claim 4, wherein obtaining the candidate mixture combinations further comprises selecting the compounds from the first plurality of library compounds that have a similarity measure greater than a threshold value.

8. The method of claim 1, wherein obtaining the candidate mixture combinations further comprises terminating the method if a second termination condition is satisfied.

9. The method of claim 1, wherein generating the model comprises generating a regression model to fit the spectrum of the unknown mixture as a function of the spectrum of each of the compounds of the candidate mixture combination.

10. The method of claim 9, wherein the regression model is based on at least one of multivariate generalized least squares regression, ridge regression, principal components based regression, partial least squares regression, principal component regression algorithm, Bayesian regression, least absolute deviation regression, least median square regression, Nadaraya Watson estimators, Kernel regression estimators, piece wise regression, local regression, and spline smoothing-based regression.

11. The method of claim 9, wherein the regression model is based on multivariate least squares regression.

12. The method of claim 9, wherein the regression model is based on non-negative multivariate least squares regression.

13. The method of claim 1, wherein the modeling metric includes at least one of a sum of squares error metric, a mean square error metric, a Durbin-Watson metric, and a mean absolute error metric.

14. The method of claim 1, wherein computing the residual spectrum comprises subtracting a fitted spectrum of the candidate mixture combination from the spectrum of the unknown mixture.

15. The method of claim 1, wherein identifying the potential compounds comprises computing a similarity measure for the second plurality of library compounds.

16. The method of claim 15, wherein the similarity measure is computed using at least one of Euclidean distance, Manhattan distance, dot product, correlation, mutual information, linear regression, principal component regression, and partial least squares regression.

17. The method of claim 15, wherein identifying the potential compounds further comprises ranking the second plurality of library compounds based on the similarity measure and selecting a pre-determined number of top ranked compounds.

18. The method of claim 15, wherein identifying the potential compounds further comprises selecting the compounds from the second plurality of library compounds that have a similarity measure greater than a threshold value.

19. The method of claim 1, wherein adding the potential compounds comprises:
    obtaining one or more new candidate mixture combinations by the addition of one or more of the potential compounds to each of the candidate mixture combinations;
    calculating a spectral error parameter for each of the new candidate mixture combinations; and
    selecting one or more candidate mixture combinations from the new candidate mixture combinations based at least in part on the spectral error parameters to generate an updated list of the candidate mixture combinations.

20. The method of claim 19, wherein the method further comprises ranking the new candidate mixture combinations based on the spectral error parameter.

21. The method of claim 20, wherein the selecting comprises selecting a pre-determined number of top ranked candidate mixture combinations.

22. The method of claim 19, wherein the selecting comprises selecting the candidate mixture combinations having the spectral error parameter less than a threshold value.

23. The method of claim 1, wherein the unknown mixture is at least one of a liquid, a solid and a powder.

24. The method of claim 1, wherein the first termination condition is completion of a fixed number of iterations.

25. The method of claim 1, wherein the first termination condition is a threshold value of the spectral error parameter.

26. The method of claim 1, wherein the first termination condition is satisfied when no significant improvement in the spectral error parameters is observed.

27. The method of claim 1, wherein the method further comprises pre-processing the spectrum of the unknown mixture by correcting the spectrum of the unknown mixture.

28. The method of claim 27, wherein the spectrum of the unknown mixture is corrected by using a Savitzky-Golay filter.

29. A system comprising:
    one or more network interfaces;
    at least one processor;
    a memory; and computer program code stored in a computer readable storage medium,
wherein the computer program code, when executed, is operative to cause the system to:
obtain one or more candidate mixture combinations by comparing the spectrum of the unknown mixture with the spectrum of each of a first plurality of library compounds;
generate a model for each of the candidate mixture combinations based, at least in part, on a modeling metric;
compute a residual spectrum corresponding to each of the candidate mixture combinations by removing the spectrum of each of the compounds of the candidate mixture combination from the spectrum of the unknown mixture;
identify one or more potential compounds by comparing each residual spectrum with the spectrum of each of a second plurality of library compounds;
add the potential compounds to the candidate mixture combinations to generate an updated list of the candidate mixture combinations; and
repeat the generating of the model, computing of the residual spectrum, identifying of the potential compounds, and adding of the potential compounds until a first termination condition is satisfied.

30. A computer program code stored in a non-transitory computer readable storage medium,
wherein the computer program code, when executed, is operative to cause the system to:
obtain one or more candidate mixture combinations by comparing the spectrum of the unknown mixture with the spectrum of each of a first plurality of library compounds;
generate a model for each of the candidate mixture combinations based, at least in part, on a modeling metric;
compute a residual spectrum corresponding to each of the candidate mixture combinations by removing the spectrum of each of the compounds of the candidate mixture combination from the spectrum of the unknown mixture;
identify one or more potential compounds by comparing each residual spectrum with the spectrum of each of a second plurality of library compounds;
add the potential compounds to the candidate mixture combinations to generate an updated list of the candidate mixture combinations; and
repeat the generating of the model, computing of the residual spectrum, identifying of the potential compounds, and adding of the potential compounds until a first termination condition is satisfied.

* * * * *